United States Patent
Bischoff et al.

[19]

[11] Patent Number: 5,816,999
[45] Date of Patent: Oct. 6, 1998

[54] FLEXIBLE CATHETER FOR THE DELIVERY OF IONIZING RADIATION TO THE INTERIOR OF A LIVING BODY

[76] Inventors: Jeffrey Bischoff, 1693 Falcon La., Loveland, Ohio 45140; Franklin H. Cocks, 5 Learned Pl., Durham, N.C. 27705

[21] Appl. No.: 899,750

[22] Filed: Jul. 24, 1997

[51] Int. Cl.$^6$ ............................................... A61N 5/00
[52] U.S. Cl. .................................................... 600/3
[58] Field of Search ................ 600/1–8; 128/897–98; 378/65, 70, 145

[56] References Cited

U.S. PATENT DOCUMENTS

| | | | |
|---|---|---|---|
| 4,821,301 | 4/1989 | Cocks et al. | 378/70 |
| 5,001,737 | 3/1991 | Lewis et al. | 378/147 |
| 5,153,900 | 10/1992 | Nomikos et al. | 378/65 |
| 5,192,869 | 3/1993 | Kumakhov | 250/505.1 |
| 5,566,221 | 10/1996 | Smith | 378/145 |

OTHER PUBLICATIONS

Charles Washington and Dennis Leaver, Introduction to Radiation Therapy, vol. I (Mosby–Year Book, Inc., St. Louis, 1996), pp. 12–24.

The Biomedical Engineering Handbook (CRC Press, Inc., Boca Raton, Florida, 1995), p. 72, pp. 9–10, p. 72.

*Primary Examiner*—John P. Lacyk

[57] ABSTRACT

The present invention is directed towards the provision of ionizing radiation from an extracorporeal source to the interior of an internal body cavity or lumen and the dispersion of this radiation across a desired area of diseased tissue. The invention consists of an extracorporeal radiation source, a flexible catheter containing at least one hollow conduit for the transportation of the radiation along a curved path, an entrance portion to the catheter for the capture of the radiation, and an x-ray dispersive closure cap at the distal end of the catheter for the dispersion of the radiation within the body cavity or lumen and onto a specific area of tissue. This invention can be used to destroy cancerous regions within the body, such as in the pulmonary system, as well as for applications in the vasculature and other internal regions of the living body.

8 Claims, 10 Drawing Sheets

FLEXIBLE CATHETER FOR THE DELIVERY OF IONIZING RADIATION TO THE INTERIOR OF A LIVING BODY

FIELD OF THE INVENTION

The present invention relates to a catheter which can transport and deposit ionizing radiation from an extracorporeal source through a curved pathway into a living body for destruction of internal tissue without this radiation passing through intervening tissue. The present invention particularly relates to the field of bronchoscopy and to the transport of x-rays into the respiratory system, where these ionizing rays can be directed for the destruction of cancerous tissue within the lung.

BACKGROUND OF THE INVENTION

The prevalence of cancers of all types, coupled with the inability of the medical community to treat successfully many incidences of cancer, gives indication of the utility of improved methods of cancer treatment, especially lung cancer. Statistics of cancer incidence in the United States, available in *Introduction to Radiation Therapy,* Volume I, edited by Washington and Leaver (Mosby-Year Book, Inc., St. Louis, 1996), pp. 12–24, indicate over 500,000 individual new cases of cancer in 1991, and almost 500,000 cancer-related deaths in 1990. Though some instances of cancer are related to an unhealthy lifestyle, many more instances are hereditary in nature or due to environmental factors beyond the victim's control. Lung cancer is the most common form of this malady affecting individuals today, accounting for 32% of all deaths attributable to cancer in 1996.

There are a wide variety of modalities available for the treatment or palliation of cancer, such as radiation therapy, chemotherapy, and cryosurgery. However, as the origin and pathogenesis of cancer remains enigmatic, no current technique of prevention or treatment is without fail, and many times there are harmful or even life-threatening consequences of the treatment. Additionally, due to the prevalence of cancer in the elderly (over 40% of all cancer cases in 1991), the best that the medical community can often do for the victim is temporary pain relief, and many times this is incomplete. However, it has long been known that cancerous cells are more sensitive to death from radiation damage than are normal cells, and this increased sensitivity has for many years been the basis of cancer treatment through ionizing radiation, especially x-radiation.

The application of the destructive powers of radiation to interior surfaces of the body is severely limited by the inability to preserve unaffected healthy tissue near the surface of the body while simultaneously destroying subcutaneous cancerous tissue or tumors. To destroy subcutaneous malignant tissue, it is typically the case that very high energy ionizing radiation, such as high energy x-rays or gamma rays, be passed through the malignant tissue from several different directions. In such a case, high energy is required so that deeply seated tumors can be reached by the ionizing energy without the deposition of a large fraction of this energy in the intervening normal tissue. In the treatment of uterine cancer, for example, the patient sometimes stands on a rotating platform and is rotated while the high energy x-ray or gamma ray radiation is passed through the tumor, which is at the axis of rotation. In this way, the cancer is continuously exposed to the ionizing radiation during patent rotation, while any given portion of normal tissue is only exposed once every revolution. It has now been discovered that by using a small hollow conduit having very smooth interior walls which have particular electron density levels, and capped at its distal end by an x-ray dispersing closure cap, relatively low energy ionizing radiation (such as relatively low energy x-radiation) can be safely transported from an extracorporeal source into a living body without affecting intervening tissue, because this ionizing radiation never interacts with this intervening tissue. The use of low energy radiation is especially advantageous because it can be entirely absorbed within the cancerous tissue, regardless of the intensity of the ionizing radiation, and so normal tissue need not be exposed to the ionizing radiation at all.

Efforts have long been made to treat subsurface tumors using extracorporeal x-ray sources. However, the necessary side effects of such treatments are the deposition of radiation into tissue between the surface of the body and the interior target area, and the concomitant diminution of x-ray intensity between the source and the target. Additionally, it has proven difficult to focus x-radiation accurately on small target areas, particularly when such targets are deep below the body surface. One method that has been discovered for circumventing these problems is to introduce an x-ray source into the body in such a way that the source is actually located at or near the core of the diseased tissue. For example, in many cases the implantation or radioactive metals such as $Co^{60}$ into a living body and the placement of this radioactive material adjacent to the cancerous mass has been attempted in order to preferentially expose the cancerous tissue to the radiation.

Another such method is described in U.S. Pat. No. 5,153,900 issued to Nomikos, et al. Nomikos presents a device consisting of a miniaturized lower power x-ray source which can be inserted into the patient's body and activated intracorporially. Electrons are generated extracorporially and directed down a rigid tube into the interior of the body, where they collide with a target to form x-radiation. This radiation is then emitted directly into the interior of the body cavity. The device disclosed by Nomikos eliminates the problem of destroying tissue between the skin and the target area, since electrons are passed through a straight, rigid, absorbing tube. However, the rigidity of the tube limits the applications of such a device to tumors which are accessible from a body orifice via a straight path. Another important failing of the device disclosed by Nomikos is this: since only a small fraction of the energy of the electrons is converted to x-rays, it is necessary to either forcibly cool the tip at which the electrons are impacted or to operate the device at very low power (intensity), and hence treatment times are excessively long. Furthermore, only electrons that have very low energies, less than a few tens of electron-volts, can be reflected and so it is not possible to use the Nomikos method if the tube is not straight, because such electrons cannot produce x-rays.

U.S. Pat. No. 5,566,221 issued to Smith, et al., discloses a device which includes an x-ray source, a rigid guidance tube, and an inflatable inelastic balloon at the distal end of the guidance tube. The rigid guidance tube serves either to allow transport of electrons to a target material which is located within the tube (thus x-radiation is generated from within the guidance tube), or to transport the x-radiation generated from an external electron-activated target to the interior organ via a straight, direct path. Once the guidance tube is inserted into the appropriate organ (such as the bladder), the balloon can be inflated, forcing the shape of the organ to coincide with that of the expanded balloon. Thus, when the electron activated x-ray source is located at the distal end of the guidance tube, x-radiation is distributed to locations along the balloon contour. However, as with Nomikos' device, the rigid, straight guidance tube severely restricts clinical applications of this device. In particular, the devices disclosed by Smith, et al., and Nomikos, et al., cannot be used for deeply seated pulmonary lesions.

U.S. Pat. No. 5,192,869 issued to Kumakhov discloses a device for the focusing of x-radiation. This design consists of a series of hollow tubes rigidly connected to each other, diverging from an x-ray source. Radiation emitted from the source will be collected in the hollow channels, and by making the initially divergent tubes collinear or convergent by curving the tubes at acceptable angles, the radiation can be directed towards a desired target. However, Kumakhov's x-ray lenses cannot transport x-radiation to interior lesions, such as those resulting from lung cancer, without the passage of these x-rays through intervening tissue, because of the massive and bulky nature of his x-ray lenses as well as its lack of a means for controllably dispersing x-rays into tissue.

Focusing of x-rays emerging at the tip of a hollow capillary was disclosed in U.S. Pat. No. 5,001,737, issued to Lewis, et al. The Lewis, et al., device is characterized by a capillary tube with a tapered outlet, such that the x-radiation in transit can be focused in cross-sectional area and thus intensity. By tapering the outlet at sufficiently small angles, similar to the curving of hollow conduits at sufficiently large radii of curvature as in the lenses disclosed by Kumakhov, all x-radiation will glance off the surfaces without being absorbed, and will thus be focused.

The device disclosed in the present invention provides a method for delivering ionizing radiation into the interior of a living body along a curved path. We have discovered that by using a flexible, hollow conduit with an interior surface of particular surface electron density and of a sufficiently small surface roughness index and with a sufficiently small interior diameter, radiation beams can be bent along highly curved paths and ionizing radiation can be introduced into any cavity of the body which can be accessed through lumens from a body opening or percutaneously. It has additionally been found that the emitted radiation can be controllably dispensed within the body cavity and the desired radiation dosage can be precisely applied to the region of interest, especially deeply seated cancers, while not affecting adjacent healthy tissue, by means of a terminal dispersive closure cap capable of defocusing and hence of dispersing the ionizing radiation.

SUMMARY OF THE INVENTION

Accordingly, taking such technical background as described above into consideration, the aim of the device of the present invention is to introduce ionizing radiation into a lumen or cavity of a living body through the use of a catheter containing at least one hollow conduit having particular properties and having a dispersive element at its distal end. Such a device, connected to an extracorporeal radiation source, can transport ionizing radiation to the interior region, thus avoiding contact of the radiation with healthy tissue between the patient's skin and the target area. A strong absorbing metal sheath (such as gold) around the hollow conduit insures that there is no measurable exposure to radiation of the body along the conduit length.

OBJECTS OF THE INVENTION

It is an object of the invention to provide a means for introducing ionizing radiation from an extracorporeal source to the interior of a living body, without affecting intervening tissue.

It is a further object of the invention to provide a conduit for ionizing radiation, which can be guided in a curve of specified dimension without failing to transmit this radiation.

It is a further object of the invention to provide a protective sheath around the ionizing radiation conduit to prevent absolutely the escape of any ionizing radiation except at the distal cap, should the conduit be bent excessively or broken.

It is a further object of the invention to provide for the selective dispersion of radiation in specific patterns from the conduit contained in the catheter.

ESSENTIAL FEATURES OF THE INVENTION

This invention discloses a catheter for the transport of ionizing radiation along a curved path and for the dispersion of this ionizing radiation in selected, specific, and known patterns. This invention is characterized by at least one flexible and hollow conduit having an internal surface of specified surface roughness index together with a particular level of surface electron density, a radiation source to supply radiation of a desired energy into the conduit, a protective sheath around the conduit to prevent the accidental escape of radiation, and a dispersive closure cap at the distal termination of the conduit to disperse the radiation.

DETAILED DESCRIPTION

The present invention will now be described more fully, with reference to the accompanying drawings. The invention may, however, be embodied in different specific forms and should not be construed as limited only to the particular embodiment set forth herein.

The invention is characterized by a flexible catheter containing an entrance portion to capture incident ionizing x-ray radiation, a conduit to carry the radiation along a curved path, and an outlet portion to disperse the ionizing x-ray radiation.

Figure 1:
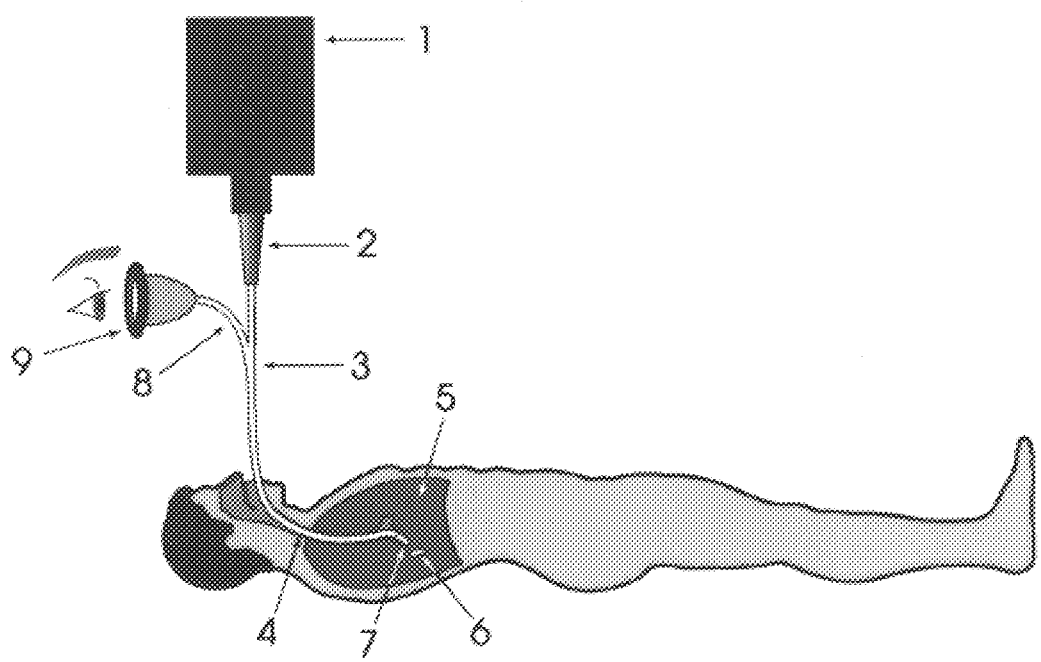
FIG. 1 shows a schematic of the catheter system for treating lung cancer, including the radiation source, entrance portion, catheter, and dispersive closure cap.
Figure 2:
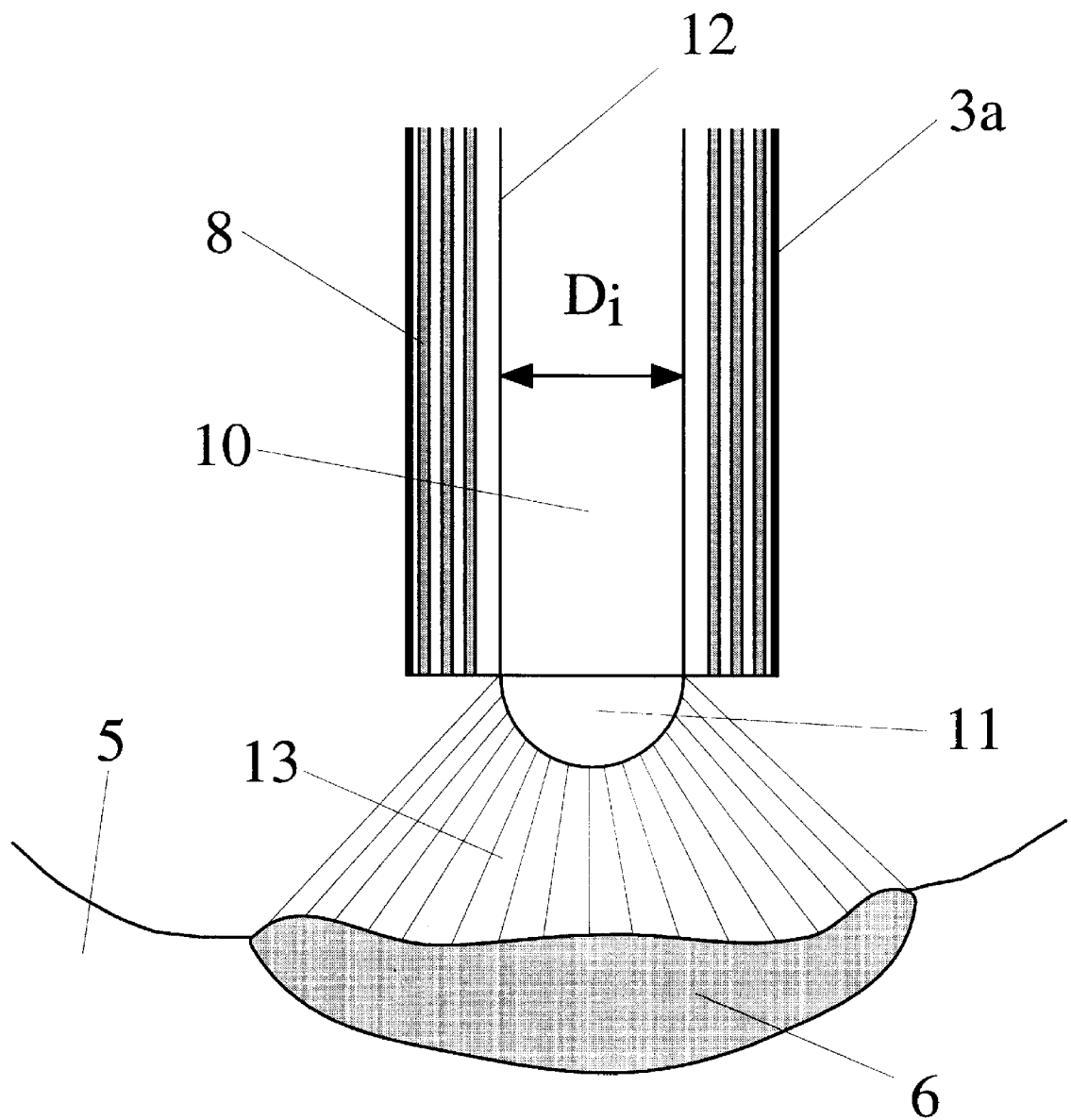
FIG. 2 is an expanded view of the distal outlet port of the catheter of FIG. 1 showing a dispersive closure cap in detail.

As shown in FIG. 1, the ionizing x-ray radiation is generated by an extracorporeal source 1 and passed through an entrance portion 2 to enter a flexible catheter 3. The flexible catheter passes through the trachea 4 and into the lung 5, and the distal end 7 of the catheter 3 is placed near and oriented towards the cancerous region 6. As shown in FIG. 2, the catheter 3 carries the x-ray conduit 10 through which the radiation is transported to a distal dispersive hemispherical closure cap 11 where the radiation exits the conduit 10 and is absorbed by the cancerous tissue 6. According to the application, a fiber-optic guidance system 8 as visualized through an eyepiece 9 may also be encompassed within the sheath, for use in directing the tip of the catheter; external visualization techniques, such as ultrasound, can also be used for orienting the catheter.

As shown in FIG. 1, the entrance portion 2 of the catheter and the extracorporeal radiation source 1 are completely enclosed to prevent harmful scattering of radiation. Radiation which enters the catheter through the entrance portion is preferably very nearly collinear with the initial direction of the catheter axis, thus permitting complete external reflection with minimal intensity loss. As shown in FIG. 2, a conduit 10 runs coaxially with the catheter 3. This catheter is enclosed by a sheath 3a, which consists of one or more flexible metallic tubes which serve to absorb the x-radiation in the event that the catheter 3 and its central conduit 10 are bent to such a small radius that the x-rays are no longer reflected from the interior surface 11 of the conduit 10. Upon reaching the distal end of the conduit 10 the ionizing x-ray radiation, which is made nearly collimated by its passage through the conduit 10, enters a radiation dispersive closure cap 11 which transforms and disperses the collimated stream of x-rays into a dispersed x-ray radiation pattern to irradiate the tumor or other diseased tissue 6 which is a portion of an otherwise normal tissue mass 5.

The distal, outlet portion of the conduit 10 has a dispersive cap 11 of particular properties to disperse the exiting radiation 13 in a controlled pattern towards the cancerous tissue 6.

PHYSICS OF THE INVENTION

Discussion of one specific application of the present invention will now be described more fully herein; however, the specifications of this invention may vary from what follows, depending on the specific desired use of the device. The particular application presented here is the introduction of x-radiation into the lung architecture for the destruction of cancerous tissue by means of the transmission of ionizing x-ray radiation along a curved path and the dispersion of this radiation as it exits the curved path in order to irradiate the tumor or other diseased tissue. The design criteria necessary for this bronchoscopy application are more stringent than many other applications, such as intestinal tumors, due to the small size of the bronchiole network, and thus other applications will allow greater flexibility in design, especially with regard to catheter dimensions.

INCIDENT RADIATION

X-radiation is generated by accelerating electrons through a voltage drop V, thus giving each electron kinetic energy $KE=eV$, where $e=1.6 \cdot 10^{-19}$ Coulombs is the charge of an electron. The energy is typically mentioned in terms of electron-volts, where one electron-volt is the energy of one electron moved through a potential difference of one volt. The electrons are directed against a metal target, such as copper, where the majority of their kinetic energy is turned into heat energy (for this reason, such a target metal is cooled by water). However, a fraction of the electron energy is converted into x-radiation. Photons comprising such x-rays can have a continuum of possible energies over photon energies less than the kinetic energy of the incident electrons. The energy, E, of a photon of wavelength, $\lambda$, is given by $E=h\nu=hc/\lambda$, where h is Planck's constant, $\nu$ is the frequency of the radiation and c is the speed of light. Thus, if all of the energy contained in one electron is converted into one single photon of radiation, the wavelength of the resulting photon can be calculated by equating the electron's kinetic energy to the photon's energy, giving $\lambda_{SWL}=hc/eV$. This value of $\lambda$ is called the short wavelength limit (SWL), as it represents the shortest wavelength (and concomitantly, the highest energy) that a photon resulting from an incident electron of known energy can possess. Using appropriate values for the constants, $\lambda_{SWL}=12.4/V$, where $\lambda_{SWL}$ is measured in Angstroms (Å) and V is measured in kilovolts (kV). This being so, it is easily seen that the shortest x-ray wavelength that can be produced by an x-ray generator operating at V=100 kV is $\lambda_{SWL}=0.124$ Å. However, along with photons of this wavelength, a continuum of x-rays of a variety of longer wavelengths (and lower energies) will also be produced.

It is in general (but not invariably) true that x-rays having longer wavelengths will be more strongly absorbed than x-rays of shorter wavelengths. Thus, for many applications, such as dental photographs, where it is desired to minimize the absorption of x-ray energy by soft, non-calcium containing tissue, higher wavelength (lower energy) x-rays must be removed. It is for this reason that one standard for dental x-ray generating machines has been that they must be operated at at least 100 kV and that the x-rays emerging from the x-ray generator must be passed through one-quarter of an inch of pure aluminum, in order to absorb the higher wavelength photons longer than 0.124 Å and to leave the SWL x-ray photons to pass through preferentially, because these ionizing x-rays will not be highly absorbed by soft tissue.

It is also to be noted that among the gamut of wavelengths which the x-ray photons (which are produced when the electrons strike the target) possess, there are certain particular wavelengths at which the corresponding photon intensities are many times greater than photon intensities corresponding to most other wavelengths. These particular wavelengths are associated with particular electron transitions between energy levels within the atoms of the target metal against which the accelerated electrons are directed. The most intense of these special wavelengths are given the designation $K_\alpha$, denoting that the x-rays are the result of electron transitions from the L energy level to the K energy level; similarly, $K_\beta$ indicates the transition occurs from the M energy level to the K energy level. In the case of a copper target, the full designation is Cu $K_\alpha$ and Cu $K_\beta$, respectively. In addition, distinct forms of Cu $K_\alpha$ x-rays can be produced, denoted by $K_{\alpha 1}$, and $K_{\alpha 2}$. These designations represent the fine structure of the L energy level in that in the L energy level, closely separated energy levels can exist. Because these special x-radiations are so much more intense than any others, it is useful in some cases to produce nearly monochromatic beams of x-rays having these particular x-ray wavelengths by special filtering or diffraction methods well known to those skilled in the art. Thus, one may speak of nearly monochromatic $CuK_{\alpha 1}$ x-radiation, whose wavelength is 1.54 Å, for example.

SHEATH AND HOLLOW CONDUIT OF PARTICULAR SURFACE ELECTRON DENSITY

In this embodiment, the external diameter of the sheath, $D_e$, is taken equal to 0.1 cm so that the catheter can be inserted into the lungs, in the manner of a bronchoscope. However, this is not to limit the use of the catheter, which can also be sized appropriately to be introduced into the major vascular system, especially those vessels in the vicinity of the heart, for appropriate applications such as the irradiation of vessel walls with x-radiation following angioplasty to prevent sclerosis due to excessive regrowth of the vessel walls. The diameters of specific interior body channels, such as air passages or blood vessels, can be found in literature such as *The Biomedical Engineering Handbook*, published by CRC Press, Inc., Boca Raton, Fla., in 1995 on pp. 9–10 and p. 72. The pulmonary system in particular is composed, in order of decreasing size, of the trachea, the bronchial tree, the bronchioles (including terminal and respiratory bronchioles), the alveolar ducts, the alveolar sacs, and finally the alveoli themselves. Typical diameters of these passages are (in centimeters) 1.8, 0.13–1.2, 0.05–0.08, 0.04, 0.04, and 0.02, respectively. Typical lengths of these passages are (in centimeters) 12.0, 0.46–4.76, 0.12–0.27, 0.08, and 0.06, respectively (excluding the alveoli). Hence, bronchoscopes are typically inserted only as far as the bronchial tree. For insertion of a catheter into bronchial tree passages, therefore, the external diameter of the catheter is preferred to be less than the internal diameter of the relaxed passages, though dilation of the passages is also possible. It is noted that the diameter of the catheter could change with its length, as appropriate for implementation.

If $D_i$ is the internal diameter of the hollow conduit and $\theta_c$ (in radians) is the critical angle for complete external reflection from the walls of the conduit, then the minimum turning radius of the catheter $R_{min}$ which allows complete x-ray reflection is given by $$R_{min} = \frac{2D_i}{\theta_c^2}. \tag{1}$$

This relationship is determined simply by the consideration of the distance along the inside of a curved tube which can be traversed by x-rays which are reflected at the angle $\theta_c$. The critical angle is dependent on both the electron density of the interior surface of the conduit and the electron density of the gas, typically air, composing the interior volume of the conduit, as reflected in the equation $$\cos\theta_c = \frac{\eta}{\eta_{air}}, \tag{2}$$

where $\eta$ (less than unity) is the index of refraction of the surface material for the ionizing x-radiation, and $\eta_{air}$ (approximately unity) is the index of refraction of air for x-rays (the index of refraction is defined to be the ratio between the speed of light in a vacuum to the speed of x-rays in the surface material). The surface whose index of refraction, $\eta$, is less than unity by the greatest amount will allow the largest critical angle of total reflection, and will permit the sharpest turning radius. An index of refraction less than unity might seem to imply that the speed of the x-rays in the material exceeds the speed of light; however, the relevant x-ray speed is the phase speed of the x-rays, not the speed of the x-rays themselves, thus special relativity is not violated for $\eta$ slightly smaller than unity. However, it will in general be the case that the deviation below unity will be relatively small since the phase velocity does not typically differ greatly from the quantum packet velocity.

Quantitatively, the index of refraction of a surface for ionizing x-rays can be written as $$\eta = 1 - \frac{\alpha}{2} + i\frac{\beta}{2} \quad (0 < \alpha, \beta \ll 1). \tag{3}$$

In Eq. (3), the symbol i indicates that the index of refraction is a complex number, and the constants $\alpha$ and $\beta$ then define the value of the complex number which quantitatively gives $\eta$. For small values of $\theta_c$, $$\theta_c = \sqrt{\alpha}. \tag{4}$$

Additionally, for a pure, single element, the value of $\alpha$ can be related to the energy E (in keV) of the incident radiation according to the relation $$\sqrt{\alpha} \approx 0.0204 \frac{\sqrt{\rho}}{E}, \tag{5}$$

where $\rho$ is the density of the element, in g/cm³. Given that the energy of each quantum wave packet of an x-ray beam is $E = hc/\lambda$, where $h = 6.626 \cdot 10^{-34}$ J·s is Planck's constant, Eqs. (4) and (5) can be combined and written as $$\theta_c \approx 0.00165 \lambda \sqrt{\rho} \tag{6}$$

where $\lambda$ is in units of Angstroms (Å). Accordingly, the minimum turning radius can be written as $$R_{min} = 7.40 \cdot 10^5 \frac{D_i}{\lambda^2 \rho}, \tag{7}$$

where $R_{min}$ and $D_i$ are in centimeters, $\lambda$ is in Angstroms, and $\rho$ is in grams per cubic centimeter.

For surfaces composed of more than one element, the critical angle for total external reflection of a surface can be calculated as $\theta_c = \sqrt{2\delta}$, as reported in U.S. Pat. No. 4,821,301, issued to Cocks and Gettliffe, where $$\delta = \frac{e^2 \lambda^2 N_{Avo}}{2\pi m c^2} \sum_n \frac{\rho_n}{A_n} \left[ Z_n + Z_{kn} \frac{\lambda^2}{\lambda_{kn}^2} \ln\left(1 - \frac{\lambda^2}{\lambda_{kn}^2}\right) \right]. \tag{8}$$

This equation is valid for surfaces composed of one or more substances, as reflected in the summation over n. In Eq. (8), $e = 4.8 \cdot 10^{-10}$ esu is the charge of an electron in electrostatic units (esu=$g^{1/2}cm^{3/2}s^{-1}$), $\lambda$ is the wavelength (in centimeters) of the incident x-radiation, $N_{Avo} = 6.022 \cdot 10^{23}$ is Avogadro's number, $m = 9.110 \cdot 10^{-28}$ g is the rest mass of an electron, and $c = 2.998 \cdot 10^{10}$ cm/s is the speed of light in a vacuum. Also, for element n, $\rho_n$ is its density (in grams per cubic centimeter), $A_n$ is its molecular weight (in grams per mole), $Z_n$ is its atomic number, $Z_{kn}$ is the number of electrons in its k energy level, and $\lambda_{kn}$ is the absorption edge (in centimeters) nearest to the incident radiation but corresponding to a lower energy than the energy of the incident radiation. Eq. (8) can be simplified by employing the quantity $$\rho_e = N_{Avo} \sum_n \frac{\rho_n}{A_n} \left[ Z_n + Z_{kn} \frac{\lambda^2}{\lambda_{kn}^2} \ln\left(1 - \frac{\lambda^2}{\lambda_{kn}^2}\right) \right], \quad (9)$$

where $\rho_e$ is the electron density and is the total number of effective electrons per cubic centimeter of the substance. Eq. (9) can be simplified when the energy of the incident radiation is far greater than the energy corresponding to the absorption edge of the $n^{th}$ surface material, that is, $\lambda << \lambda_{kn}$; in these situations, the quantity in brackets in Eq. (9) can simply be replaced by $Z_n$. Eq. (9) is further simplified when the surface is composed of only one element, giving $$\rho_e = \frac{N_{Avo} \rho Z}{A}. \quad (10)$$

Eq. (9) can be inserted back into Eq. (8) to give $$\delta = \frac{e^2 \lambda^2 \rho_e}{2\pi mc^2}. \quad (11)$$

The minimum turning radius can be calculated by inserting Eq. (11) into the equation $\theta_c = \sqrt{2\delta}$, then inserting this value of $\theta_c$ into Eq. (1) and using known values of the physical constants; these manipulations give $$R_{min} = \frac{2\pi mc^2 D_i}{e^2 \lambda^2 \rho_e} = 2.23 \cdot 10^{13} \frac{D_i}{\lambda^2 \rho_e} \quad (12)$$

where $\lambda$ is in units of centimeters and $R_{min}$ and $D_i$ have the same units of length. Note that Eq. (12) reduces to Eq. (7) when the surface is composed of a single element and the incident radiation is of a much lower wavelength than that of the absorption edge of the surface element. In these situations, Eq. (10) is used in Eq. (12), and using the approximation $A/Z \approx 2$, $$R_{min} = 7.41 \cdot 10^{-11} \frac{D_i}{\lambda^2 \rho}. \quad (13)$$

This equation reduces essentially to Eq. (7) when it is recognized that in Eq. (13), the wavelength is in centimeters whereas in Eq. (7), the wavelength is in Angstroms.

It has been discovered that surfaces which have electron density values in the range $5 \cdot 10^{21} < \rho_e < 5 \cdot 10^{25}$ can be produced on the interior of the hollow conduit to reflect x-radiation down the conduit. For example, the effective electron density of a pseudo-cermet surface comprised of silver and quartz, which can be produced by diffusing heavy metals such as silver into glass, for Cr $K_{\alpha 1}$ incident x-radiation (2.29 Å), can be approximately $1.05 \cdot 10^{24}$ electrons per cubic centimeter and a concomitant minimum x-ray turning radius of 405.1 cm, for a conduit with an internal diameter of $D_i = 0.01$ cm.

Five different potential incident radiation sources may be considered to provide examples of the minimum turning radii that can be produced without limiting the invention thereto: Al ($K_{\alpha 1} = 8.34$ Å), Ti ($K_{\alpha 1} = 2.75$ Å), Cr ($K_{\alpha 1} = 2.29$ Å), Cu ($K_{\alpha 1} = 1.54$ Å), and Mo ($K_{\alpha 1} = 0.29$ Å). As examples, materials with two different dissimilar surface electron densities can be considered to compose the surface from which the radiation is reflected: $SiO_2$ ($\rho_e = 6.54 \cdot 10^{23}$ electrons/cm$^3$, $\rho = 2.2$ g/cm$^3$) and Ag ($\rho_e = 3.21 \cdot 10^{24}$ electrons/cm$^3$, $\rho = 10.5$ g/cm$^3$). TABLE 1 gives values of $\theta_c$ and $R_{min}$ for both surfaces for these various radiation sources when the radiation passes along a hollow conduit with an internal diameter of $D_i = 0.01$ cm.

TABLE 1

Critical angle for total external reflection and minimum turning radius for various types of incident radiation on surfaces with different surface electron densities.

| | $\rho e (\cdot 10^{23}/cm^3)$ | Al $K_{\alpha 1}$ | Ti $K_{\alpha 1}$ | Cr $K_{\alpha 1}$ | Cu $K_{\alpha 1}$ | Mo $K_{\alpha 1}$ |
|---|---|---|---|---|---|---|
| $\theta_c$ (deg) | 6.54 | 1.17 | 0.39 | 0.32 | 0.22 | 0.04 |
| | 32.1 | 2.55 | 0.84 | 0.70 | 0.47 | 0.09 |
| $R_{min}$ (cm) | 6.54 | 49.0 | 450.9 | 650.2 | 1437.8 | 40544.4 |
| | 32.1 | 10.0 | 91.9 | 132.5 | 292.9 | 8260.5 |

From TABLE 1, it is clear that higher-wavelength radiation gives a smaller minimum turning radius and a concomitant larger critical angle for total external reflection. As a preferred embodiment, Al $K_{\alpha 1}$ radiation into a conduit whose interior walls contain $3.21 \cdot 10^{24}$ electrons per cubic centimeter, produced by diffusing a heavy metal such as silver into the wall surface, will allow a minimum turning radius of $R_{min} = 10.0$ cm and will have a critical angle of $\theta_c = 2.55°$.

Figure 3:
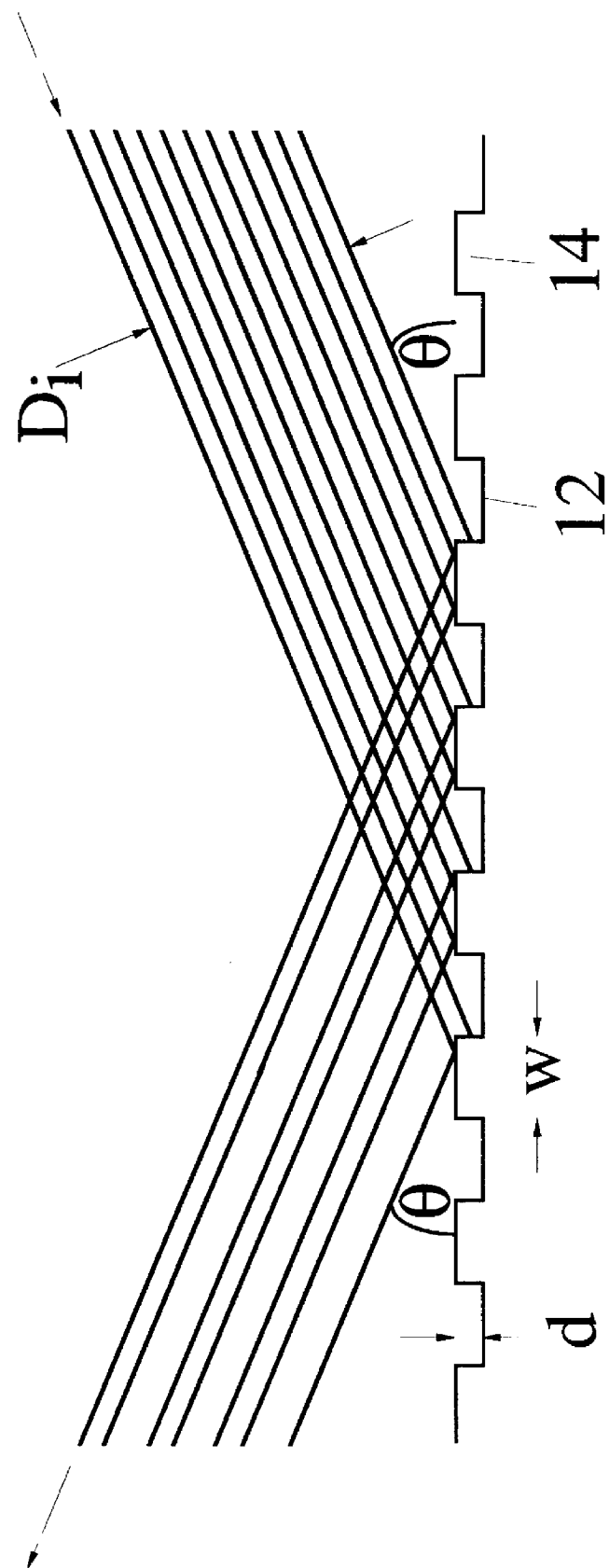
FIG. 3 shows the geometry used to calculate the magnitude of the maximum permissible interior surface roughness index of the catheter.

The interior surface 12 of the hollow conduit must be sufficiently smooth that a minimal amount of radiation intensity is lost into the wall due to surface irregularities. There are many models for surface irregularities, one of which is shown schematically in FIG. 3. The degree of precision of this surface can be calculated using the following assumptions: irregularities in the interior surface can be modeled as steps 14 of height, d, and width, w, on the interior surface 12 of the conduit 10, that there are many steps within each contact between the x-ray beam and the conduit wall, and that the intensity of the beam lost during each contact is small relative to the intensity of the reflected beam. The degree of precision can be calculated in terms of a surface roughness index (SRI), defined as SRI$\equiv$d/w. In FIG. 3, $D_i$ is the internal diameter of the conduit 10 and $\theta$ is the angle at which the x-rays are incident upon and reflected from the interior surface 12. FIG. 3 shows this angle greatly exaggerated. In reality, the incident and reflection angles are at most a few degrees. If the incident angle is greater than some critical value $\theta_c$, then these x-rays are not reflected but penetrate the interior surface 12.

Figure 4:
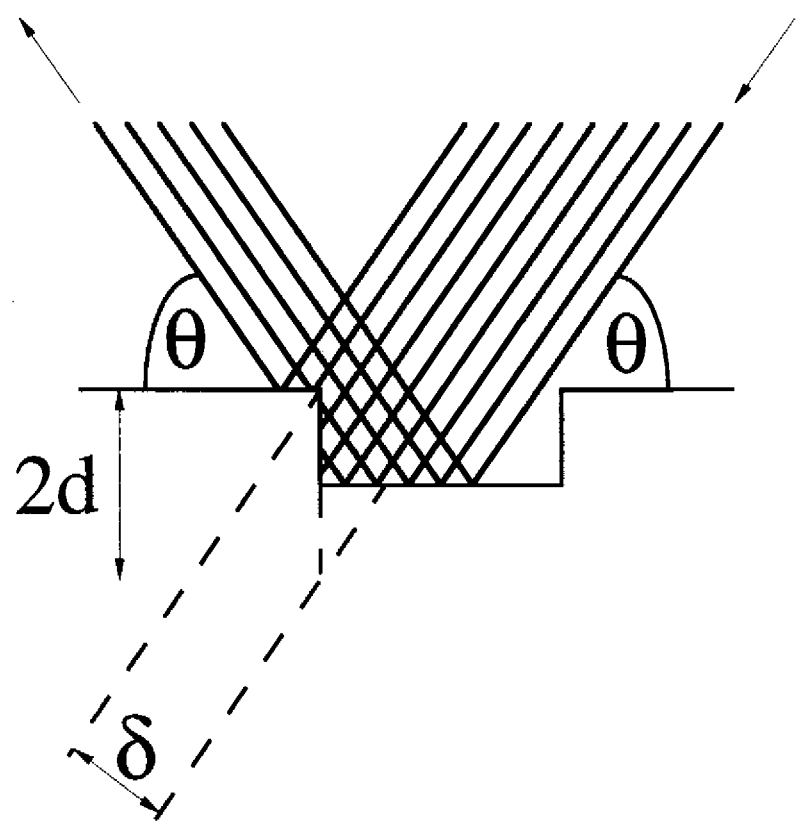
FIG. 4 shows one mechanism for the loss of radiation into a wall with a surface roughness.
Figure 5:
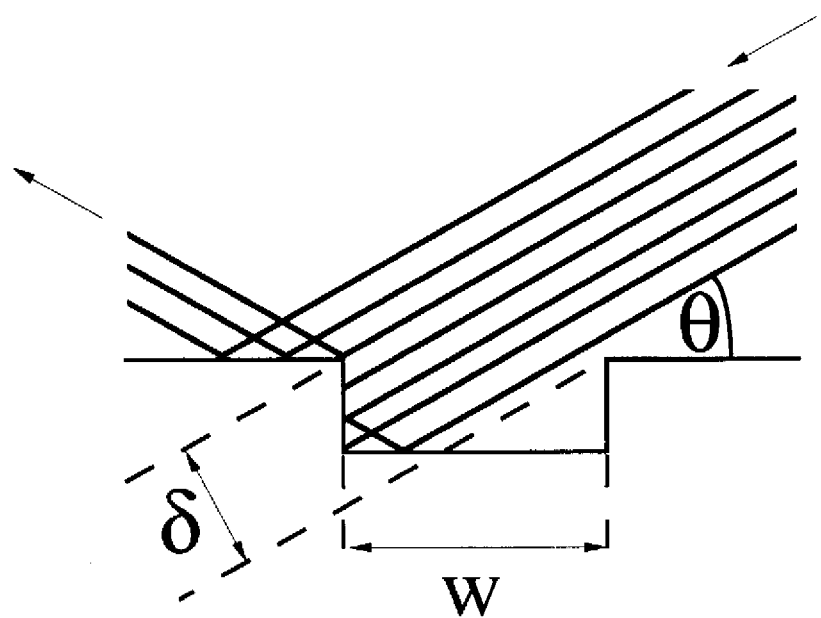
FIG. 5 shows a second mechanism for the loss of radiation into a wall with a surface roughness.

It might be thought that there would be two independent situations which could model the x-ray beam's contact with the interior surface 12, depending on the relative sizes of $D_i$, d, w, and $\theta$ (the incident angle of the x-ray radiation), as shown in FIG. 4 and in FIG. 5, which illustrate these two cases. For both cases, the beam will encounter a number $n = D_i/(2w \sin \theta)$ of steps 14 in the interior surface 12 on average. The first situation (FIG. 4) is valid when the beam hits at such an angle that reflected radiation from the surface 12 which is at the bottom of the valleys formed by the steps 14 in the interior surface 12 will not necessarily be lost; that is, when $\tan \theta \geq 2d/w$. In such a situation, the fraction, $\delta$, of the diameter of the beam lost per hit per step is given by $\delta = 2d \cos \theta$. Therefore, $\delta \geq w \sin \theta$. The alternative situation (FIG. 5) occurs when all of the beam which enters each valley is lost, or when $\tan \theta < 2d/w$. In this case, the beam loss per hit per step is given by $\delta = w \sin \theta$, and accordingly $\delta > 2d \cos \theta$. The total number of contacts N between the beam and the wall will nominally depend on $\theta$, L (the total length of the catheter), and $D_i$; that is, $N = (L/D_i) \tan \theta$. Given a catheter length of L=50 cm, an interior diameter $D_i = 0.01$ cm of the hollow conduit, and an incident angle of $\theta = 2.5°$ (less than the critical angle of Al $K_{\alpha 1}$ radiation on silver) the number of hits is $N \approx 220$. The total loss $\delta_T$ in beam diameter from entrance to exit is therefore $$\delta_T = Nn\delta = \left(\frac{L}{D_i}\tan\theta\right)\left(\frac{D_i}{2w\sin\theta}\right)\delta = \frac{L\delta}{2w\cos\theta}. \quad (14)$$

Since the intensity of an x-ray beam is proportional to the cross-sectional area of the beam, the fractional intensity of the beam which is lost through the catheter (relative to the incident intensity) is then $$\delta I = \frac{I_i - I_o}{I_i} = \frac{D_i^2 - (D_i - \delta_T)^2}{D_i^2} = \frac{L\delta}{wD_i\cos\theta}\left(1 - \frac{L\delta}{4wD_i\cos\theta}\right). \quad (15)$$

Using the values of L, $D_i$, and $\theta$ above, and assuming a maximum permissible loss of 5% of the initial beam intensity, it is found that $\delta/w \leq 1.01 \cdot 10^{-5}$. This result implies the condition $\tan\theta \geq 2d/w$, and therefore the model of beam loss as shown in FIG. 4 is the appropriate model for the small angles of reflection considered here. Accordingly, the loss per hit per step is $\delta = 2d \cos\theta$ and the surface roughness index, $SRI = d/w$, is limited according to $SRI \leq 5.10 \cdot 10^{-6}$. Therefore, the average depth of the irregularities must be on the order of $10^5$ times smaller than the average length of the irregularities.

DISTAL DISPERSIVE CLOSURE CAP

For treatment of tumors on the interior of body cavities or lumens, it is necessary for the x-radiation to diverge from the distal end of the catheter. With no means for dispersion, x-rays which are transmitted down the conduit will exit the distal end of the conduit in a direction approximately parallel to the axis of the catheter at the distal end; the maximum angular deviation from parallel is given by the angle, $\theta_c$. They will thus be approximately collimated, and will not be suitable for the treatment of large cancerous masses.

It has now been discovered that x-ray fluorescence and also x-ray diffraction may be used to disperse the ionizing radiation. In one dispersive closure cap embodiment, the cap is composed of a fluorescent medium covering the exit of the conduit. As has been discovered, such an x-ray fluorescent cap can absorb incident, monochromatic, unidirectional radiation of one wavelength and emit fluorescent radiation of a higher wavelength (and concomitant lower energy) in dispersed directions. We have now found that optimum materials and thicknesses for such a fluorescent cap is determined by maximum transmission of fluorescent radiation and that this maximum can be calculated for simple geometries. Dispersion of the x-ray beam can also be achieved by means of diffraction from a distal cap rather than by fluorescence.

For an incident beam which is monochromatic and unidirectional, the intensity $I_{in}$ of the x-radiation is found to decrease as it passes through a fluorescent closure cap according to the linear first order differential equation $$\frac{dI_{in}}{I_{in}} = -\mu dz \quad (16)$$

where $\mu$ is the linear absorption coefficient (which can be in units of reciprocal centimeters) for the incident radiation and z is oriented parallel to the incident radiation. As the incident radiation is absorbed, fluorescent radiation with a longer wavelength and concomitant lower energy is produced. The intensity of the fluorescent radiation in any given direction, in spherical coordinates $(\rho, \theta, \phi)$, has now been found to be given by $$\frac{\partial I_{fl}}{\partial \rho} = -K\frac{\partial I_{in}}{\partial \rho} - \mu_2 I_{fl}, \quad (17)$$

where K is a measure of the energy transfer between the incident and fluorescent (emitted) radiation and $\mu_2$ is the linear absorption coefficient of the material of the distal dispersion element for the fluorescent radiation $I_{fl}$. (In this spherical coordinate system, $\phi$ is measured relative to the z-axis defined previously.) The sign in front of the $\partial I_{in}$ term must be negative because, according to Eq. (16), $\partial I_{in}$ is negative but causes a positive increment $\partial I_{fl}$ in the emitted fluorescent radiation. Similarly, the sign in front of the $\mu_2$ term is negative because absorption decreases the intensity of the fluorescent radiation.

Eq. (16) can be solved for the intensity of the incident radiation throughout the cap. The solution is $$I_{in} = I_o \exp(-\mu z) \quad (18)$$

where $I_o$ is the uniform intensity of the radiation at the leading edge of the material (z=0). Therefore, from Eq. (17) and using the coordinate transformation $z = \rho \cos\phi$, $$\frac{\partial I_{fl}}{\partial \rho} = \mu K I_o \cos\phi \exp(-\mu\rho\cos\phi) - I_{fl}\mu_2. \quad (19)$$

The solution to this equation is $$I_{fl}(\rho, \phi) = \frac{\mu K I_o \cos\phi}{\mu_2 - \mu\cos\phi} \exp(-\mu\rho\cos\phi) + B\exp(-\mu_2\rho). \quad (20)$$

where B is a constant of integration to be determined from the boundary conditions. To determine B, note that as the size of the material gets small, $\rho$ approaches zero, giving $$\lim_{\rho \to 0} I_{fl}(\rho, \phi) = \frac{\mu K I_o \cos\phi}{\mu_2 - \mu\cos\phi} + B. \quad (21)$$

For this to be zero, as it must be since there will be no fluorescent radiation without the appropriate medium, $B = -\mu K I_o \cos\phi/(\mu_2 - \mu\cos\phi)$. Thus, $$I_{fl}(\rho, \phi) = \frac{\mu K I_o \cos\phi}{\mu_2 - \mu\cos\phi}[\exp(-\mu\rho\cos\phi) - \exp(-\mu_2\rho)]. \quad (22)$$

This equation transformed back into cylindrical coordinates is $$I_{fl}(r, z) = \frac{\mu K I_o z}{\mu_2\sqrt{r^2 + z^2} - \mu z}[\exp(-\mu z) - \exp(-\mu_2\sqrt{r^2 + z^2})]. \quad (23)$$

The average intensity of the radiation leaving a given closure cap through a given portal can be calculated using Eq. (23) (recall that the only assumption used to derive Eq. (23) was that the incident radiation was uniformly $I_o$ at z=0). One configuration of this device is that the cap is a cylindrical plug, and that the distal end of the cap is exposed to the interior of the body cavity, whereas all radiation exiting the cap through the sides is absorbed into the gold sheath. A second configuration of this device is a cap of the same shape as before, but the distal end of the cap is sealed whereas radiation is allowed to exit through a side portal. A third configuration is a hemispherical cap where the radiation exits over the entire hemispherical surface. Illustrative calculations will be performed for all three of these configurations.

In the first configuration, the dispersive closure cap is a cylindrical plug of length L and diameter $D_i$ (equal to the inner diameter of the hollow conduit) with a portal of area $A_{end}$ at its distal end through which radiation exits into the body cavity. The average intensity of the fluorescent radiation emitted into the body cavity through the distal end is given by $$\bar{I}_{fl,end} = \frac{2\pi}{A_{end}} \int_0^{D_i/2} I_{fl}(r, z = L) r dr \qquad (24)$$

$$= \frac{8KI_0}{\gamma^2} \left[ \exp(-\lambda) \int_0^{\gamma/2} \frac{\bar{r} d\bar{r}}{\alpha\sqrt{1+\bar{r}^2} - 1} - \int_0^{\gamma/2} \frac{\bar{r} \exp(-\lambda_2 \sqrt{1+\bar{r}^2})}{\alpha\sqrt{1+\bar{r}^2} - 1} d\bar{r} \right],$$

where $\bar{r} = r/L$, $\alpha = \mu_2/\mu$, $\gamma = D_i/L$, $\lambda = \mu L$, and $\lambda_2 = \mu_2 L$.

In this first configuration, the length of the plug is contained within the sheath so that radiation cannot pass into the body in a direction normal to the axis of the conduit, but rather can only pass through the termination of the plug at its distal end. In some situations it may be desirable to have the ionizing radiation directed normally to the axis of the conduit. In this second configuration, the dispersive closure cap is shaped as in the first configuration (a cylindrical plug), but the exit portal is located on the side of the cap, rather than at its distal tip. This enables radiation to exit in a direction perpendicular to the axis of the catheter. To determine the average intensity of the fluorescent radiation emitted in this configuration for an exit portal of width W and length L (equivalent to the length of the closure cap), Eq. (23) can be used to calculate $$\bar{I}_{fl,side} = \frac{W}{A_{side}} \int_0^L I_{fl}\left(r = \frac{D_i}{2}, z\right) dz \qquad (25)$$

$$= \frac{KI_0\gamma}{2} \left[ \int_0^{2/\gamma} \frac{\bar{z}}{\alpha\sqrt{1+\bar{z}^2} - \bar{z}} \exp\left(-\frac{\kappa \bar{z}}{2}\right) d\bar{z} - \int_0^{2/\gamma} \frac{\bar{z}}{\alpha\sqrt{1+\bar{z}^2} - \bar{z}} \exp\left(-\frac{\kappa_2}{2}\sqrt{1+\bar{z}^2}\right) d\bar{z} \right]$$

where $\bar{z} = 2z/D_i$, $\kappa = \mu D_i$, and $\kappa_2 = \mu_2 D_i$.

In the third configuration, a hemispherical dispersive closure cap of diameter $D_i$ (equivalent to the internal diameter of the hollow conduit) is used, where fluorescent radiation is allowed to exit through any portion of the hemisphere. The average intensity of the emitted fluorescent radiation can be calculated as $$\bar{I}_{fl,he} = \frac{1}{A} \int_A I_{fl}\left(\rho = \frac{D_i}{2}, \phi\right) dA \qquad (26)$$

where $A = \pi D_i^2/2$ is the surface area of the hemispherical cap, $dA = (D_i^2/4) \sin\phi d\theta d\phi$ is the differential area element in spherical coordinates, and Eq. (22) is used to give $I_{fl}$ in spherical coordinates. Accordingly, Eq. (23) reduces to $$\bar{I}_{fl,he} = \qquad (27)$$

$$KI_0 \int_0^{\pi/2} \frac{\sin\phi\cos\phi}{\alpha - \cos\phi} \left[ \exp\left(-\frac{\kappa}{2}\cos\phi\right) - \exp\left(-\frac{\kappa_2}{2}\right) \right] d\phi.$$

Figure 6:
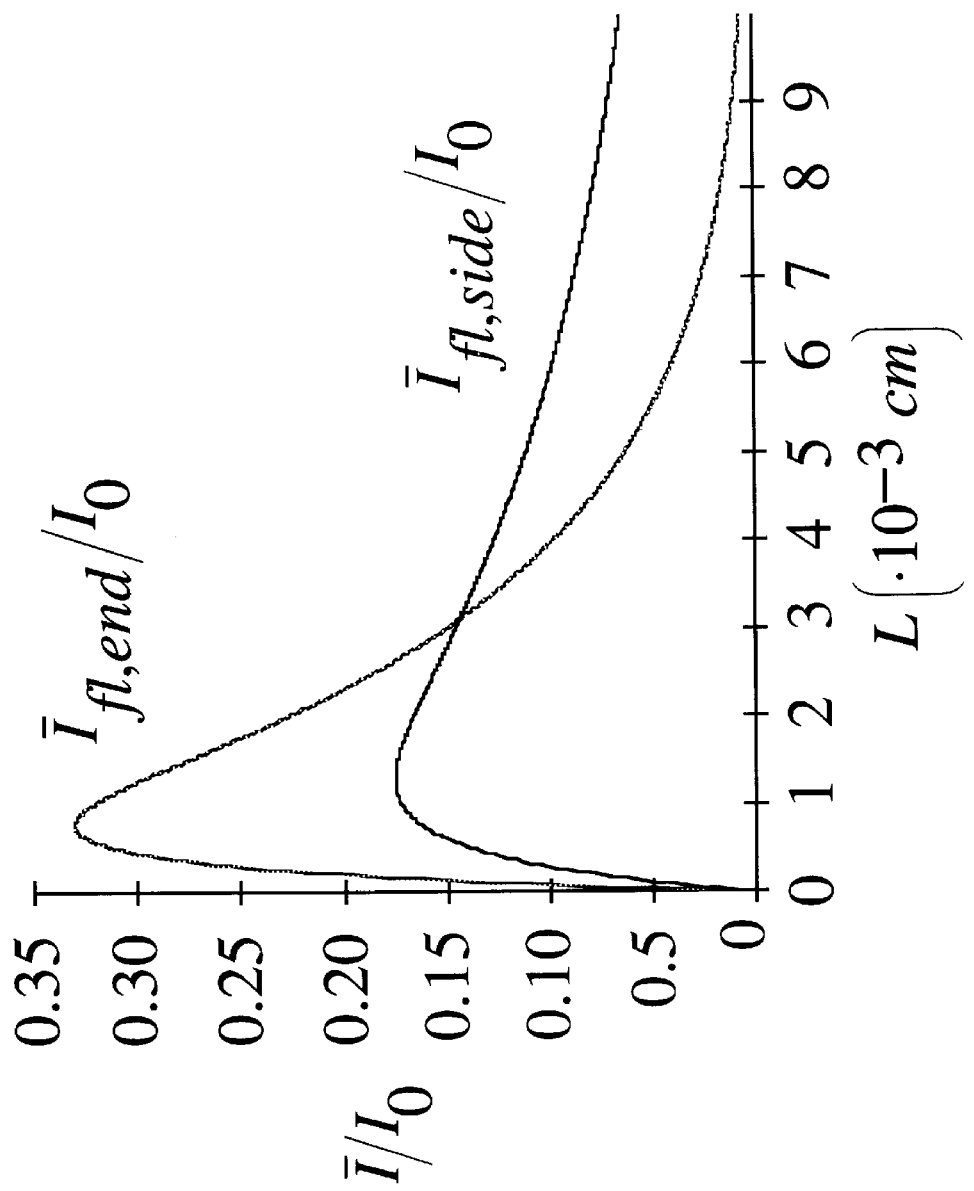
FIG. 6 shows a plot of $\bar{I}_{fl,end}/I_o$ (the average intensity of fluorescent radiation exiting a cylindrical dispersive closure cap through its distal tip, divided by the incident radiation intensity) vs. L (the length of the cylindrical distal dispersive closure cap) and $\bar{I}_{fl,side}/I_o$ (the average intensity of fluorescent radiation exiting a cylindrical dispersive closure cap through a side portal, divided by the incident radiation intensity) vs. L, where the incident radiation is Cr $K_{\alpha 1}$ radiation and the dispersive closure cap contains Ti.

To evaluate Eqs. (24) and (25), a preferred embodiment of the device can be given in which chromium $K_{\alpha 1}$ (2.29 Å) is the incident radiation and the closure cap is made from Ti (K absorption edge of 2.50 Å). The mass absorption coefficient of Cr $K_{\alpha 1}$ in Ti is $\mu/\rho_o = 571.4$ cm$^2$/g and the normal density of Ti is $\rho_o = 4.51$ g/cm$^3$, giving a linear absorption coefficient of $\mu = (\mu/\rho_o) \cdot \rho_o = 2577$/cm. (The use of the mass absorption coefficient for Ti enables the calculation of the linear absorption coefficient for Ti of any concentration; for example, if Ti is dispersed in a plastic medium approximately transparent to x-radiation such that the local density of Ti is $\rho_{Ti} < \rho_o$, then the linear absorption coefficient is $\mu = (\mu/\rho_o) \cdot \rho_{Ti}$.) The fluorescent radiation (Ti $K_{\alpha 1}$, 2.75 Å) has a mass absorption coefficient of $\mu/\rho_o = 111.4$ cm$^2$/g in Ti, giving a linear absorption coefficient of $\mu_2 = (\mu/\rho_o) \cdot \rho_o = 502.4$/cm. Thus, the ratio $\alpha = \mu_2/\mu = 0.195$. The internal diameter is assumed to be $D_i = 0.01$ cm, giving $\kappa = 25.77$ and $\kappa_2 = 5.024$. The only dimension left unknown is the length L of the plug, which is also necessary to calculate $\gamma$, $\lambda$, and $\lambda_2$. The values of the intensity can be calculated for a variety of plug lengths, in order to maximize the emitted intensity for each of the two configurations. FIG. 6 shows a plot of $\bar{I}_{fl,end}/I_o$ vs. L and $\bar{I}_{fl,side}/I_o$ vs. L, for K=1. As shown in the figure, when the exit portal is located at the distal tip of the cylindrical plug, maximum average emitted fluorescent intensity of $\bar{I}_{fl,end}/I_o = 0.3306$ is obtained at L=0.0008 cm; when the exit portal is located along the side of the cylindrical plug, maximum average emitted fluorescent intensity of $\bar{I}_{fl,side}/I_o = 0.1751$ is obtained at L=0.0013 cm.

Figure 7:
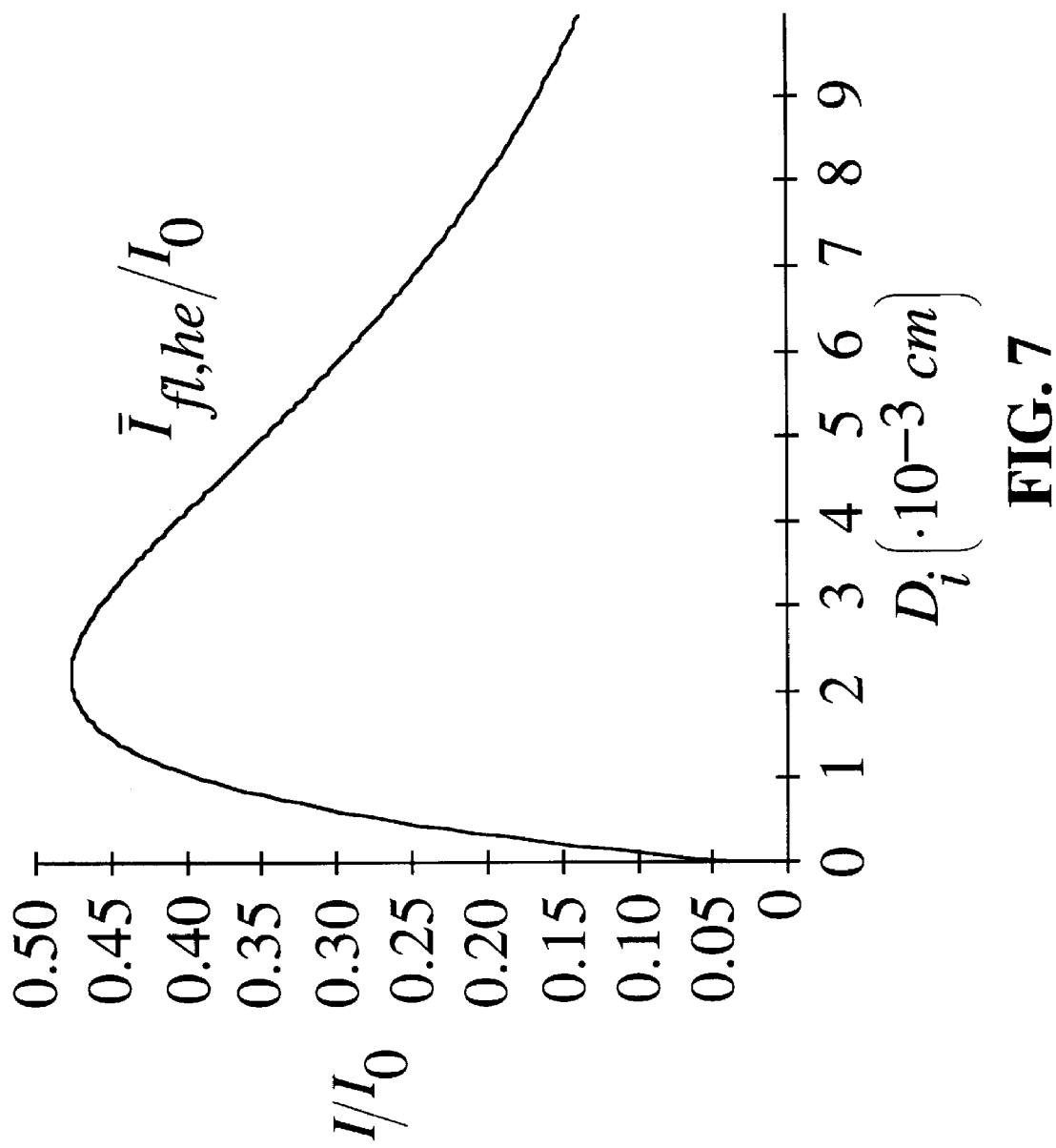
FIG. 7 shows a plot of $\bar{I}_{fl,he}/I_o$ (the average intensity of fluorescent radiation exiting a hemispherical dispersive closure cap, divided by the incident radiation intensity) vs. $D_i$ (the internal diameter of the hollow conduit), where the incident radiation is Cr $K_{\alpha 1}$ radiation and the closure cap contains Ti.

To evaluate Eq. (27), a preferred embodiment of the device can be given in which Cr $K_{\alpha 1}$ is again the incident radiation, and the dispersive closure cap is again made from Ti. The internal diameter of the hollow conduit, and therefore the diameter of the hemispherical closure cap, can be varied in order to determine the size of the cap which maximized the average emitted fluorescent intensity. FIG. 7 shows a plot of $\bar{I}_{fl,he}/I_o$ vs. $D_i$, for K=1. As shown in the figure, a maximum averaged emitted fluorescent intensity of $\bar{I}_{fl,he}/I_o = 0.4762$ is obtained at $D_i = 0.0023$ cm.

The material of the cap can be selected such that it absorbs as much of the incident radiation as possible, allowing only the fluorescent radiation to pass through. We have now discovered that the wavelength of the incident radiation must be smaller than the K absorption edge of the material to give optimum cap performance. Materials which can be used for the cap include any element whose K absorption edge is greater than the wavelength of the incident radiation. If Cr $K_{\alpha 1}$ (2.29 Å) is the x-radiation used, a good material to use for the cap would be Ti with a K absorption edge of 2.50 Å.

This model has been developed for the case of fluorescence. However, it will be appreciated that other modalities for the dispersion of the x-ray beam may also be devised using diffraction, refraction, reflection, or scattering of the x-ray beam.

The depth that the fluorescent radiation or other dispersed x-ray radiation will penetrate into the diseased tissue before its intensity is reduced to insignificant levels can be calculated for each type of fluorescent radiation which might be used. For example, if the dispersive closure cap is made using Ti, present as TiO$_2$, the linear absorption coefficient of the tissue (assumed to be water) for the fluorescent Ti $K_{\alpha 1}$ (2.75 Å) can be calculated as $$\mu_{H_2O} = \left(\frac{\mu}{\rho_0}\right)_H \rho_H + \left(\frac{\mu}{\rho_0}\right)_O \rho_O \qquad (28)$$

where $(\mu/\rho_o)_H$ and $(\mu/\rho_o)_O$ are the mass absorption coefficients of Ti $K_{\alpha 1}$ radiation in hydrogen (0.4323 cm$^2$/g) and oxygen (64.79 cm$^2$/g), respectively, and $\rho_H$ and $\rho_O$ are the densities in water of hydrogen and oxygen, respectively.

Given that the density of water is $\rho_{H_2O} \approx 1$ g/cm$^3$, the density of hydrogen in water can be calculated as $$\rho_H = \rho_{H_2O} \cdot \left( \frac{2 \text{ g H}}{16 \text{ g H}_2\text{O}} \right) = 0.125 \text{ g/cm}^3. \tag{29}$$

Similarly, the density of oxygen in water can be calculated to be $\rho_O = 0.875$ g/cm$^3$. These two densities sum, of course, to the density of the water itself, one gram per cubic centimeter. Thus, for Ti $K_{\alpha 1}$, $\mu_{H_2O} = 57.64$/cm. Accordingly, using Eq. (18), the radiation will pass through 0.12 cm of tissue before being diminished by 99.9%. In this manner, the radiation will be effectively limited to this depth and so even if the cancer is only a surface cancer, exposure of underlying normal tissue will be very limited. Of course, thick cancers will need multiple treatments as the irradiated layers slough away or are reabsorbed.

RADIATION DOSAGE TO INTERIOR OF BODY CAVITY

Figure 8:
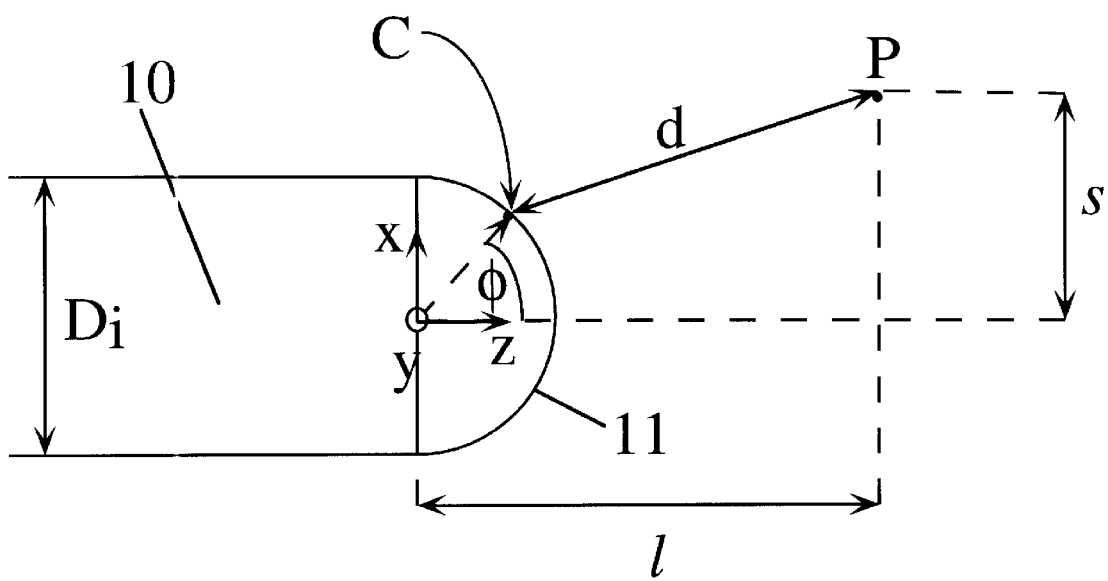
FIG. 8 shows the geometry near the dispersive closure cap utilized to determine the total fluorescent radiation intensity at a point separate from the cap.

In clinical treatment, it is useful if the total radiation dosage that will be distributed to the interior of a body cavity or lumen can be calculated for a given cavity surface. Using a fluorescent, hemispherical, x-ray dispersive closure cap described above, consider the intensity at a point P (s,0,l), where the center of the cap is located at (0,0,0) and the z-axis is oriented directly out from the catheter (by symmetry, the orientation of the x- and y-axes are not important). With reference to FIG. 8, the square of the distance from P to a point C ($D_i \sin \phi \cos \theta/2$, $D_i \sin \phi \sin \theta/2$, $D_i \cos \phi/2$) on the dispersive closure cap surface is $$d^2 = \left( \frac{D_i}{2} \sin\phi\cos\theta - s \right)^2 + \left( \frac{D_i}{2} \sin\phi\sin\theta \right)^2 + \left( \frac{D_i}{2} \cos\phi - l \right)^2. \tag{30}$$

Figure 9:
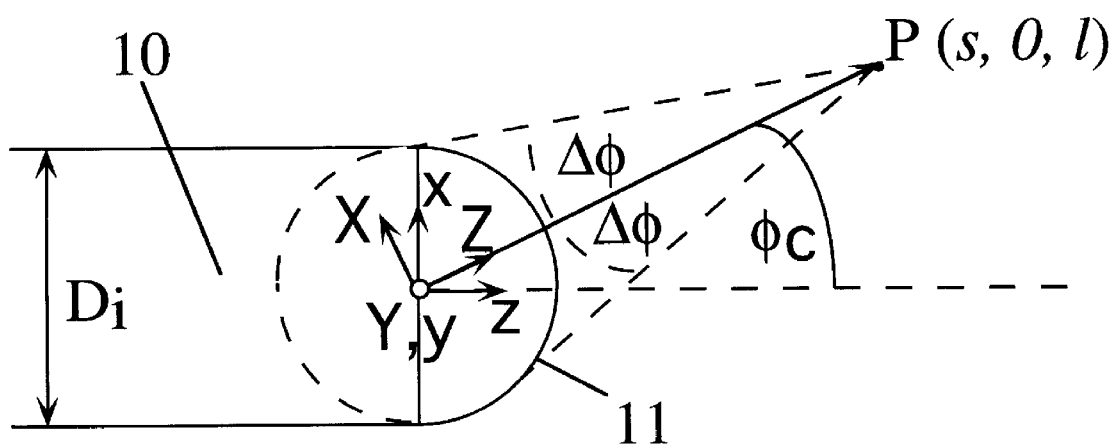
FIG. 9 shows the surface portions of a hemispherical dispersive closure cap which will irradiate a point separate from the cap.

Accordingly, the total fluorescent intensity incident on P from all points on the dispersive closure cap surface is $$\hat{I}_{fl,cyl} = \int_A \frac{I_{fl}(D_i/2, \phi)}{2\pi d^2} dA, \tag{31}$$

where the integration is performed over all portions of the hemisphere which have a direct line of sight with P. Upon proper substitutions, Eq. (31) becomes $$\hat{I}_{fl,cyl} = \frac{KI_0 D_i^2}{8\pi} \int_\phi \int_\theta \frac{\sin\phi\cos\phi[\exp(-\kappa\cos\phi/2) - \exp(-\kappa_2/2)]}{(\alpha - \cos\phi)(D_i^2/4 + s^2 + l^2 - D_i s \sin\phi\cos\theta - D_i l\cos\phi)} d\theta d\phi, \tag{32}$$

where the range of values of $\theta$ and $\phi$ are to be determined from the specifics of the requisite geometry. In general, a point beyond a sphere will have a direct line of sight with a portion of the sphere within a well defined circle on its surface. With reference to FIG. 9, this circle (parallel to the y-axis) is defined by its center located at an angle $\phi_c = \tan^{-1}(s/l)$, its span defined by the angle $$\Delta\phi = \sin^{-1}[D_i/(2\sqrt{s^2 + l^2})],$$

and its distance $D_i/2$ from the origin. The equation of this circle can be determined by rotating the initial coordinate system (x,y,z) through an angle $\phi_c$ about the y-axis, according to the transformation $$\begin{bmatrix} X \\ Y \\ Z \end{bmatrix} = \begin{bmatrix} \cos\phi_c & 0 & \sin\phi_c \\ 0 & 0 & 0 \\ -\sin\phi_c & 0 & \cos\phi_c \end{bmatrix} \begin{bmatrix} x \\ y \\ z \end{bmatrix}, \tag{33}$$

where (X,Y,Z) represents the transformed coordinate system. In this new system, the circle is located perpendicular to the Z-axis, and its equation is $$X^2 + Y^2 = \frac{D_i^2}{4} \cos^2\Delta\phi. \tag{34}$$

Eq. (34) can be transformed back to the initial spherical coordinate system, and $\theta$ can be solved for in terms of $\phi$ giving $$\cos\theta = \cot\phi\cot\phi_c \pm \frac{\sin\Delta\phi}{\sin\phi\sin\phi_c}. \tag{35}$$

The smallest positive and negative values of $\theta$ (referred to as $\pm\theta_{max}$) which satisfy this equation become the bounds which define the surface of interest (the portion of the hemispherical dispersive closure cap which has a direct line of sight with the point P) for any value of $\phi$. When Eq. (35) cannot be solved for $\theta_{max}$, all values of $\theta$ should be used, that is, $\theta_{max} = \pi/2$. Accordingly, the limits on $\theta$ are $-\theta_{max} \leq \theta \leq \theta_{max}$, and, to ensure the integration is performed only over a hemisphere, the limits on $\phi$ are $\phi_{min} = \max(-\pi/2, \pi/2 - \phi_c - \Delta\phi) \leq \phi \leq \phi_{max} = \min(\pi/2, \pi/2 + \phi_c - \Delta\phi)$. Applying these limits and performing the integration over $\theta$, Eq. (32) becomes $$\hat{I}_{fl,cyl} = \frac{KI_0 D_i^2}{4\pi} \int_{\phi_{min}}^{\phi_{max}} \frac{\sin 2\phi[\exp(-\kappa\cos\phi/2) - \exp(-\kappa_2/2)]}{(\alpha - \cos\phi)\sqrt{a(\phi)^2 - b(\phi)^2}} \tan^{-1}\left[ \sqrt{\frac{a(\phi) - b(\phi)}{a(\phi) + b(\phi)}} \tan\left( \frac{\theta_{max}}{2} \right) \right] d\phi \tag{36}$$

where $a(\phi) = D_i^2/4 + s^2 + l^2 - D_i \cos \phi$ and $b(\phi) = -D_i s \sin \phi$. Eq. (36) can be solved numerically to give the total fluorescent intensity at any point external to the hemispherical x-ray dispersive closure cap.

Similarly, the total intensity from fluorescent radiation exiting a cylindrical dispersive closure cap with a portal at its distal end at a point P (s,0,l) external to the catheter can be calculated. Assuming the center of the distal surface of the dispersive closure cap is located at (0,0,0), the distance from a point C (x,y) = (r cos $\theta$, r sin $\theta$) on the distal surface to P is $$d^2 = (r\cos\theta - s)^2 + (r\sin\theta)^2 + l^2. \tag{37}$$

Accordingly, the total fluorescent intensity at point P from all points on the dispersive cap is $$\hat{I}_{fl,hem} = \int_A \frac{I_{fl}(r, L)}{2\pi d^2} dA \tag{38}$$

where $I_{fl}$ is calculated according to Eq. (23), $dA = r \, dr \, d\theta$ is the differential area element, and the integration is performed over the entire distal surface of the dispersive closure cap.

Upon substitution and simplification, $$\hat{I}_{fl,hem} = KI_0 \int_0^{\gamma/2} \frac{\exp(-\lambda) - \exp(-\lambda_2 \sqrt{\bar{r}^2+1})}{(\alpha\sqrt{\bar{r}^2+1} - 1)\sqrt{(\bar{r}^2+\bar{s}^2+\bar{l}^2)^2 - 4\bar{r}^2\bar{s}^2}} \bar{r}d\bar{r} \quad (39)$$

where $\bar{r}$, $\alpha$, $\gamma$, $\lambda$ and $\lambda_2$ are as defined as before, $\bar{s}=s/L$, and $\bar{l}=l/L$. Eq. (39) can be solved numerically to give the total fluorescent intensity at any point external to the cylindrical x-ray dispersive closure cap which has an exit portal at its distal end.

Figure 10:
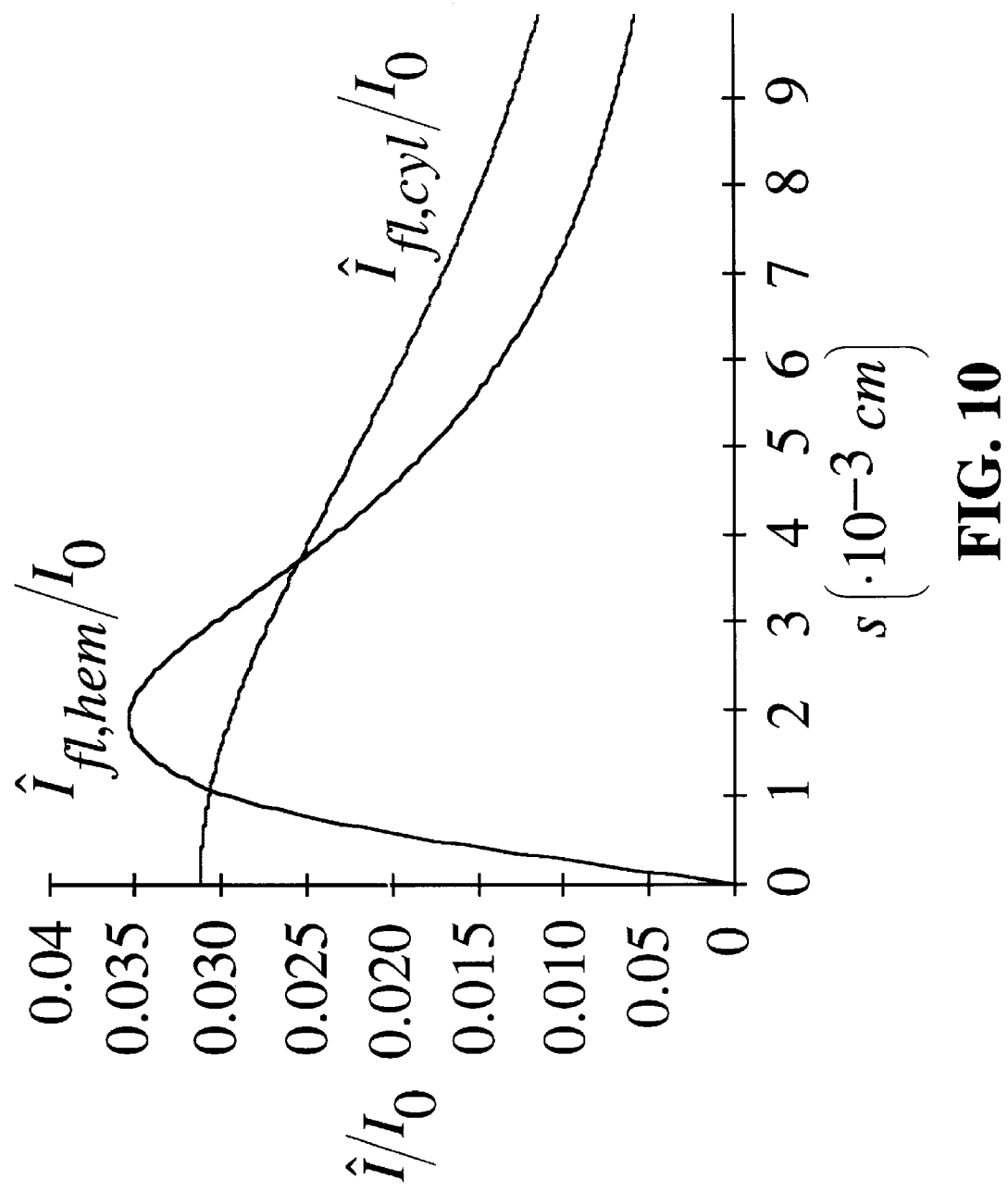
FIG. 10 shows a plot of the total fluorescent intensity incident on a screen perpendicular to the axis of the conduit vs. the distance from the conduit axis, for a cylindrical dispersive closure cap and a hemispherical closure cap, utilizing the principle of x-ray fluorescence to cause dispersion.

FIG. 10 shows a plot of the total fluorescent intensity incident on a screen perpendicular to the axis of the conduit vs. the distance s from the conduit axis, for fluorescent radiation exiting a cylindrical dispersive closure cap ($\hat{I}_{fl,cyl}$) and a hemispherical closure cap ($\hat{I}_{fl,hem}$), according to Eqs. (36) and (39), respectively. In both cases, the incident radiation was Cr $K_{\alpha 1}$ radiation and the dispersive closure cap contained Ti. To calculate $\hat{I}_{fl,cyl}$, the dimensions of the cylindrical plug were L=0.0008 cm and $D_i$=0.01 cm, and the screen was located a distance l=0.03 cm from the distal end of the dispersive closure cap. To calculate $\hat{I}_{fl,hem}$, the diameter of the hemispherical cap was set to be $D_i$=0.0023 cm and the screen was located a distance l=0.0033 cm from the center of the hemispherical cap.

PREFERRED EMBODIMENT

To target cancerous tissue within the pulmonary system, a preferred embodiment provides for the delivery and dispersion of x-radiation into the lungs using a flexible catheter inserted through the appropriate air passages. An extracorporeal x-ray machine sending electrons at an accelerating voltage of 100,000 volts to a Cr target whose $K_{\alpha 1}$ x-ray radiation wavelength is 2.29 Å is preferably used in this embodiment, together with a vanadium filter, whose absorption edge is 2.27 Å. This vanadium filter serves to filter the x-rays being produced by this machine so that only the $K_{\alpha 1}$ radiation is primarily present in the ionizing x-ray beam which exits the filter. In other embodiments where a continuum of radiation is desired, the filter can be removed. In addition, the accelerating voltage can be varied between 1000 and 1,000,000 volts. In addition also, any metallic electron target material can be chosen as may be needed for the particular cancer to be treated in a particular location. The filtered radiation is directed into an entrance portion of a conduit which has an inside surface with a surface electron density preferably of $\rho_e$=3.21·10$^{24}$ electrons per cubic centimeter produced by diffusing an element with a high atomic number, preferably silver, into the walls of the conduit. This entrance portion is oriented to capture this ionizing x-ray radiation. In other cases, elements with atomic numbers above 47 can be diffused into the wall of the conduit to produce surface electron densities from 5·10$^{21}$ to 5·10$^{25}$ electrons per cubic centimeter as may be needed for particular applications. The inside surface of the conduit preferably has an average surface roughness index less than 0.01. The conduit is enclosed within a gold sheath preferably having a wall thickness of 0.01 centimeters. In some other cases the sheath thickness may be as thin as 0.001 centimeters or as thick as 0.1 centimeters, and in such a case multiple sheaths may be used to increase flexibility while still retaining a total gold thickness through the several sheaths of 0.01 centimeters. In this preferred embodiment, the sheath has an outer diameter of 0.2 cm with a radial thickness of 0.05 cm. In other cases the sheath may have an outer diameter not greater than 2 centimeters and not less than 0.01 centimeters in internal diameter. The conduit can range in internal diameter from not greater than 0.5 centimeters to not less than 0.001 centimeters. In each case the inner diameter of the sheath must be larger than the outer diameter of the conduit. If multiple conduits are used, the inner diameter of the sheath must be large enough to accommodate all of the conduits. In the case of multiple conduits, it is necessary that these multiple conduits not be rigidly connected so that flexibility is retained. In a preferred case the inner diameter of 0.01 cm can allow a 13.4 cm turning radius while still permitting the transport of ionizing x-ray radiation. In this preferred embodiment a hemispherical x-ray dispersing closure cap of rutile is used to terminate the conduit at its exit portion. Rutile is a particular form of $TiO_2$ and has a density of 4.25 g/cm$^3$. This hemispherical cap of rutile is put onto the distal end of the conduit and produces a dispersion of fluorescent radiation when irradiated with the Cr $K_{\alpha 1}$ radiation. In the present case, the catheter is inserted through the trachea to the bronchial tree, to the appropriate site for treatment.

In this preferred embodiment, a thin fiber optic cable is in addition inserted into the sheath, along with the x-ray conduit, for visualization of the target area. Light from the fiber optic cable is directed to illuminate an area within the body cavity which is congruent with the area which is to be irradiated by the fluorescent x-ray dispersing closure cap.

We claim:

1. A flexible catheter for delivery of ionizing x-ray radiation to the interior of a living body, said catheter consisting essentially of at least one flexible sheath, at least one flexible hollow conduit contained in said sheath, at least one ionizing radiation dispersing closure cap terminating said conduit, and means for generating said ionizing x-ray radiation, said flexible catheter being inserted into said living body, said flexible hollow conduit having an entrance portion and an exit portion, said entrance portion being oriented to capture said ionizing radiation, said radiation produced using accelerating voltages between 1000 and 1,000,000 volts, said sheath being less than 2 centimeters in external diameter and no smaller than 0.01 centimeters in internal diameter, said sheath enclosing said flexible hollow conduit along its length, said flexible hollow conduit having an interior surface with an average surface roughness index less than 0.01 and having a surface electron density at its interior surface between 5·10$^{21}$ and 5·10$^{25}$ electrons per cubic centimeter, whereby said radiation is passed by total reflection along said conduit and exits through said dispersing closure cap, said dispersing closure cap covering said exit portion of said conduit, whereby said radiation which passes through said dispersing closure cap is dispersed before delivery to said interior surface of said living body.

2. A flexible catheter for delivery of ionizing radiation to an interior surface of a living body according to claim 1, wherein said sheath is substantially composed of metal with an atomic number higher than 47.

3. A flexible catheter for delivery of ionizing radiation to an interior surface of a living body according to claim 1, wherein said conduit has an internal diameter of not less than 0.001 cm and not more than 0.5 cm.

4. A flexible catheter for delivery of ionizing radiation to an interior surface of a living body according to claim 1, wherein said conduit has an internal diameter which decreases along its length from said entrance portion to said exit portion.

5. A method for the delivery of extracorporeal radiation to the interior of a living body for the treatment of disease, said extracorporeal radiation passing through a flexible catheter with an entrance portion and an exit portion according to the principle of total reflection, said flexible catheter consisting essentially of at least one flexible sheath, at least one flexible hollow conduit contained in said sheath, at least one ionizing radiation dispersing closure cap at said distal end of said sheath, and extracorporeal means for generating said ionizing radiation, said method consisting of the steps of inserting said flexible catheter into said living body, energizing said means for generating said ionizing radiation, directing said ionizing radiation into said exit portion of said catheter, delivering said ionizing radiation through said conduit according to the principle of total reflection, and dispersing said ionizing radiation with said dispersing closure cap, whereby said radiation is dispersed to said interior of said living body.

6. The method according to claim 5 wherein the said interior of said living body is contained within a lung.

7. The method according to claim 5 wherein the said interior of said living body is contained within a blood vessel.

8. The method according to claim 5 wherein said dispersing closure cap disperses said radiation by means of x-ray fluorescence.

* * * * *